United States Patent [19]

Evans

[11] Patent Number: 4,520,204

[45] Date of Patent: May 28, 1985

[54] METHOD FOR PREPARATION OF AROMATIC ETHER IMIDES AND FOR CATALYST RECOVERY THEREIN

[75] Inventor: Thomas L. Evans, Schenectady, N.Y.

[73] Assignee: General Electric Company, Schenectady, N.Y.

[21] Appl. No.: 488,461

[22] Filed: Apr. 25, 1983

[51] Int. Cl.³ ............................................. C07D 209/48
[52] U.S. Cl. .................................... 548/461; 548/476; 548/481
[58] Field of Search ....................... 548/461, 476, 481

[56] References Cited

U.S. PATENT DOCUMENTS

| | | | |
|---|---|---|---|
| 4,247,464 | 1/1981 | Relles et al. | 548/476 |
| 4,257,953 | 3/1981 | Williams et al. | 548/461 |
| 4,273,712 | 6/1981 | Williams | 548/461 |

*Primary Examiner*—Mark L. Berch
*Assistant Examiner*—William A. Teoli, Jr.
*Attorney, Agent, or Firm*—William H. Pittman; James C. Davis, Jr.; James Magee, Jr.

[57] ABSTRACT

The yield of aromatic ether imides prepared by reacting a substituted phthalimide (such as 4-nitro-N-methylphthalimide) with an alkali metal salt of a hydroxyaromatic compound (such as the disodium salt of bisphenol A) in the presence of a phase transfer catalyst is improved by conducting the reaction in o-dichlorobenzene as diluent. When the reaction mixture is subsequently extracted with water and/or aqueous alkali, o-dichlorobenzene can also be used in recovery of the phase transfer catalyst from the aqueous phase by extraction thereof. Such recovery is improved by dissolving a substantial amount of inorganic salt in the aqueous phase and by conducting the o-dichlorobenzene extraction at elevated temperatures.

13 Claims, No Drawings

METHOD FOR PREPARATION OF AROMATIC ETHER IMIDES AND FOR CATALYST RECOVERY THEREIN

This invention relates to the preparation of aromatic ether imides. In its broadest sense, the invention is an improvement in a method for preparing such imides by the nucleophilic displacement reaction of at least one substituted phthalimide with at least one alkali metal salt of a hydroxyaromatic compound in an organic diluent in the presence of a phase transfer catalyst, said improvement comprising at least one of the following options:

(A) conducting said displacement reaction in o-dichlorobenzene as diluent, and (B) effecting aqueous extraction of the reaction mixture and subsequently recovering a substantial amount of said phase transfer catalyst from the aqueous phase by extraction with o-dichlorobenzene.

Aromatic ether imides are useful as chemical intermediates in a number of processes. For example, 2,2-bis[4-(N-methylphthalimide-4-oxyphenyl]propane (hereinafter "bisphenol A bisimide") is used in the preparation of polyetherimides. In the preferred processes for the preparation of aromatic ether imides, an alkali metal salt of a hydroxyaromatic compound undergoes a nucleophilic displacement reaction with a substituted phthalimide. The reaction is usually effected in a relatively non-polar organic diluent such as benzene, toluene, xylene, chlorobenzene, tetrahydrofuran, octane, acetonitrile or the like in the presence of a phase transfer catalyst, typically a tetraalkylammonium salt. Reference is made to U.S. Pat. Nos. 4,257,953 and 4,273,712, the disclosures of which are incorporated by reference herein. A frequently used diluent for this reaction is toluene.

The reaction mixture containing the prepared aromatic ether imide also contains extraneous material such as unreacted substituted phthalimide, phase transfer catalyst and various inorganic salts formed in the displacement reaction. Separation of these extraneous materials from the product is typically effected by aqueous extraction with one or more of water and dilute aqueous alkali.

The use of toluene (or similar diluents) in this process has certain disadvantages. One is a result of the rather low solubility in toluene of certain aromatic ether imides, particularly bisphenol A bisimide, as a result of which it is necessary to use complex material handling techniques or a large excess of toluene. Also, it has been discovered that the reaction is somewhat slower in toluene than is desirable. Moreover, many phase transfer catalysts are either ineffective in toluene or only sparingly soluble therein and thus are lost in the aqueous extraction process, since it is impossible to remove them from the aqueous phase by toluene extraction for recycling.

A principal object of the present invention, therefore, is to provide an improved method for the preparation of aromatic ether imides.

A further object is to provide an improved diluent for use in such preparation.

A further object is to provide a method for increasing the rate of the displacement reaction yielding the aromatic ether imide.

Still anothr object is to increase the versatility of the reaction by enabling the use of a wider variety of phase transfer catalysts therein.

A still further object is to improve the economics of the process by enabling recovery and recycling of the phase transfer catalyst.

Other objects will in part be obvious and will in part appear hereinafter.

For the most part, the substituted phthalimides useful in the method of this invention have the formula

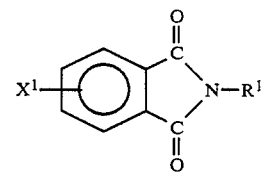

wherein $R^1$ is hydrogen, an alkyl radical having from 1 to 8 carbon atoms or an aryl radical having from 6 to 13 carbon atoms and $X^1$ is nitro or halo (i.e. fluoro, chloro, bromo, or iodo and preferably chloro or bromo). Most often, $R^1$ is a $C_{1-4}$ alkyl radical and especially methyl and $X^1$ is nitro.

The salt which undergoes a nucleophilic displacement reaction with the substituted phthalimide is an alkali metal (e.g., lithium, sodium or potassium and preferably sodium) salt of at least one hydroxyaromatic compound. Suitable hydroxyaromatic compounds are illustrated by those having the formula $Q(OH)_n$, wherein Q is an aromatic hydrocarbon-based radical and n is 1 or 2.

The term "aromatic hydrocarbon-based radical" as used herein denotes an aromatic radical free from ethylenic and acetylenic unsaturation, having a carbon atom directly attached to the remainder of the molecule and having predominantly hydrocarbon character within the context of this invention. Such radicals include the following:

(1) Hydrocarbon radicals; that is, aromatic and mixed aliphatic-aromatic and alicyclic-aromatic radicals. Such radicals are known to those skilled in the art; examples are phenyl, tolyl, xylyl, phenylene, tolylene, xylylene, 1,4-naphthylene, 1-5-naphthylene, p,p'-biphenylene and 2,2-(p,p'-diphenylene)propane (all isomers being included).

(2) Substituted hydrocarbon radicals; that is, radicals containing non-hydrocarbon substituents which, in the context of this invention, do not alter the predominantly hydrocarbon character of the radical. Those skilled in the art will be aware of suitable substituents; examples are halo, alkoxy (especially lower alkoxy), carbalkoxy and alkyl sulfone.

(3) Hetero radicals; that is, radicals which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

For the most part, not more than three substituents or hetero atoms will be present for each 10 carbon atoms in the hydrocarbon-based radical.

The radical Q is a monovalent or divalent aromatic hydrocarbon-based radical. It is most often a divalent radical derived from benzene or a substituted benzene, biphenyl or a substituted biphenyl, or a diphenylalkane which may contain substituents on one or both aromatic radicals. The following radicals are preferred as Q:

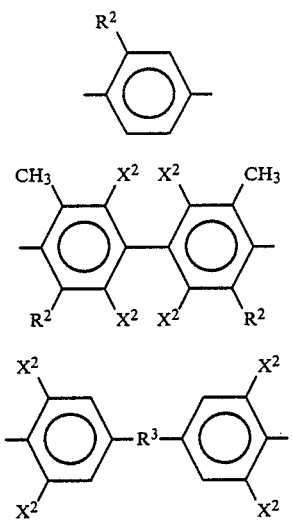

wherein each $R^2$ is independently hydrogen or methyl, $R^3$ is a straight-chain or branched alkylene radical containing 1–5 carbon atoms and is most often the isopropylidene radical, and each $X^2$ is independently hydrogen or halogen (usually chlorine or bromine). Mixtures of the foregoing formulas are also contemplated. Especially preferred is the radical derived from bisphenol A [i.e., 2,2′-bis(4-hydroxyphenyl)propane] by the removal of both hydroxy groups therefrom, and having the third of the above formulas wherein $R^3$ is isopropylidene and each $X^2$ is hydrogen.

Various classes of compounds may be used as phase transfer catalysts in the method of this invention. These include, for example, quaternary ammonium and phosphonium compounds and crown ethers. Illustrative phase transfer catalysts are tetraethylammonium bromide, tetraethylammonium acetate, tetrabutylammonium bromide, tetraphenylphosphonium bromide and 18-crown-6 (1,4,7,10,13,16-hexaoxacyclooctadecane). Mixtures of said catalysts can also be used. The particularly preferred phase transfer catalysts are tetraalkylammonium halides, tetraarylphosphonium halides and crown ethers. Most preferred is tetrabutylammonium bromide.

According to the present invention, one or preferably both of two options are employed in the preparation of the aromatic ether imide. Option A is the use of o-dichlorobenzene as a diluent for the displacement reaction. Other than the identity of the diluent, the reaction conditions are substantially the same as those disclosed in the aforementioned U.S. Pat. No. 4,273,712; namely, a reaction temperature from about 25° to about 150° C., a proportion of reactants of about 5–150% by weight based on diluent, a mole ratio of substituted phthalimide to hydroxyaromatic compound salt of about 2:1, and a ratio of equivalents of phase transfer catalyst to hydroxyaromatic compound salt from 0.005 to 2.

Two of the advantages of option A are that it enables recovery of the aromatic ether imide in greater yield after a shorter reaction time, and that it enables the use of a wider variety of phase transfer catalysts than is possible when toluene is the diluent. When toluene is used, optimum yields of bisphenol A bisimide are obtained when the phase transfer catalyst is tetrabutylammonium bromide, and no other catalysts afford the bisimide in comparable yields. In o-dichlorobenzene, on the other hand, roughly equivalent yields (85–90% after 5 hours) are obtained using tetrabutylammonium bromide, tetraethylammonium bromide, tetraphenylphosphonium bromide and 18-crown-6.

The alkali metal salt is typically prepared in an aqueous medium by reacting the hydroxyaromatic compound with the corresponding alkali metal hydroxide or equivalent reagent. When it is so prepared, it must be dried prior to reaction with the substituted phthalimide. Drying is often most conveniently effected after suspension of the alkali metal salt in o-dichlorobenzene. The drying method may be contact with any of various drying agents known in the art (e.g., calcium hydride, calcium chloride, magnesium sulfate, molecular sieves). Another useful drying procedure is azeotropic removal of water by distillation. When this method is used, it may be necessary to minimize foaming of the wet o-dichlorobenzene suspension of the alkali metal salt by such expedients as rapid stirring, vigorous refluxing or use of a high concentration of the alkali metal salt in the aqueous system.

If option A is not employed, the diluent maay be any one or more of those listed hereinabove and in U.S. Pat. No. 4,273,712, or any other suitable diluent.

Option A of the method of this invention is illustrated by the following examples.

EXAMPLE 1

Bisphenol A, 5 grams (0.022 mole), was added under nitrogen, with stirring, to a solution of 1.76 gram (0.044 mole) of sodium hydroxide in 25 ml. of water. The solution of the bisphenol A disodium salt was added dropwise to 250 ml. of boiling o-dichlorobenzene. The resulting suspension was dried by heating under reflux over calcium hydride for 8 hours. There were then added 9.04 grams (0.044 mole) of 4-nitro-N-methylphthalimide and 0.22 gram (0.0066 mole) of tetrabutylammonium bromide. The mixture was heated for 12 hours at 110° C., with stirring. Water, 200 ml., was then added and the organic layer was separated and extracted twice with 200 ml. of 1% aqueous sodium hydroxide solution and once with 200 ml. of water. The o-dichlorobenzene was removed from the organic phase by vacuum evaporation to yield 96% of the theoretical amount of the desired bisphenol A bisimide. The product was shown by high pressure liquid-liquid chromatography to be substantially pure; it melted at 147° C.

EXAMPLE 2

The rates of reaction of the disodium salt of bisphenol A with 4-nitro-N-methylphthalimide in o-dichlorobenzene and toluene were measured by the following procedure: A mixture of 0.4 gram (0.0026 mole) of biphenyl (used as an internal standard), 0.66 gram (0.00243 mole) of bisphenol A disodium salt and 0.023 gram (0.0007 mole) of tetrabutylammonium bromide in 4 ml. of the dry solvent was heated at 110° C. for 15 minutes, after which 1 gram (0.00485 mole) of 4-nitro-N-methylphthalimide was added. The reaction was allowed to proceed at 110° C. and was monitored periodically by high pressure liquid-liquid chromatography. The results are given in the following table.

| Time, min. | Yield of bisphenol A bisimide, % (by weight) | |
| --- | --- | --- |
| | Toluene | o-Dichlorobenzene |
| 15 | 40 | 63 |
| 30 | 53 | 74 |
| 45 | 65 | 82 |
| 60 | 72 | 93 |
| 90 | 100 | 100 |

It is apparent that the reaction is substantially faster in o-dichlorobenzene than in toluene.

Option B of the method of this invention relates to the recovery of phase transfer catalyst for recycle. The phase transfer catalyst is one of the materials removed when the reaction mixture is extracted with water and/or dilute aqueous alkali, and it has customarily been lost at that stage since the catalysts customarily used are not sufficiently soluble in toluene to enable extraction therewith and recovery. However, these catalysts are soluble in o-dichlorobenzene, and therefore it is possible to use that liquid as an extractant for recovery of the phase transfer catalyst from the aqueous phase and subsequently to recycle the recovered catalyst in solution in o-dichlorobenzene. The amount of o-dichlorobenzene used for extraction is most often about 1-2 volumes per volume of aqueous phase.

When extraction is effected by merely agitating the aqueous phase with o-dichlorobenzene, catalyst recovery is low, often less than 1%. Various operations may be employed to recover a substantial amount of catalyst, typically at least about 20%, by extraction. For example, recovery may be substantially increased by continuous countercurrent liquid-liquid extraction.

It has also been found that dissolution of a substantial proportion of inorganic salt in the aqueous phase prior to extraction with o-dichlorobenzene materially increases the amount of phase transfer catalyst recovered. For optimum recovery, the amount of inorganic salt dissolved in the aqueous phase should be at least about 35 grams and preferably at least about 75 grams per 100 ml.

Any water-soluble inorganic salt may be used for this purpose, provided it does not undergo an undesirable reaction with the phase transfer catalyst. (As explained hereinafter, anion exchange is usually not an undesirable reaction.) The most inexpensive and readily available salts are the preferred ones; these are illustrated by the alkali metal (preferably sodium) chlorides and nitrites. The latter are particularly useful because they are readily obtainable as by-products in the reaction of the nitrophthalimide with the alkali metal salt of the hydroxyaromatic compound, and also because they are soluble in water in large proportions.

The effect of inorganic salts in the aqueous system is illustrated by the results of extraction with 100 ml. of o-dichlorobenzene at 25° C. of an aqueous system containing 1 gram of tetrabutylammonium bromide per 100 ml. In the absence of other salts, less than 1% of the phase transfer catalyst is recovered by such extraction. Saturation of the aqueous phase with sodium chloride (which has a solubility at 25° C. of about 37 grams per 100 ml.) results in an approximately 23% recovery. Dissolution in the aqueous phase of sodium nitrite at 48 grams per 100 ml. and at saturation (about 81.5 grams per 100 ml. at 25° C.) results in recoveries on the order of 35% and 70%, respectively.

When the inorganic salt is sodium nitrite, anion exchange occurs and the actual compound recovered by extraction is predominantly tetrabutylammonium nitrite. It is within the scope of the invention to recycle it as such for further use or to reconvert it to the halide or other suitable salt for recycle.

Still another method of improving catalyst recovery is to increase the temperature of extraction. Temperatures above about 65° C. are preferred, and those above about 75° C. are most preferred. In general, there is no advantage in a higher extraction temperature than about 95° C.

The improvement afforded by an increase in temperature alone is apparent from the fact that o-dichlorobenzene extraction of an aqueous tetrabutylammonium bromide solution as described above which also contains 48 grams of sodium nitrite per 100 ml. results in approximately a 60% recovery of catalyst when conducted at 67° C. Further increases in recovery may be effected by saturating the aqueous phase with inorganic salt at the higher temperature. Thus, saturation with sodium nitrite at temperatures of 67° C. or higher increases catalyst recovery to about 80% or greater, while saturation with sodium chloride at 78° C. increases recovery to almost 65%. When toluene is substituted for o-dichlorobenzene as an extractant, catalyst recovery is under no conditions higher than about 5%.

What is claimed is:

1. In a method for preparing an aromatic ether imide by the nucleophilic displacement reaction of at east one substituted phthalimide with at least one alkali metal salt of a hydroxyaromatic compound in an organic diluent in the presence of a phase transfer catalyst followed by aqueous extraction of the reaction mixture, the improvement which comprises: effecting said extraction with an aqueous phase containing a substantial proportion of inorganic salt dissolved therein, and subsequently recovering a substantial amount of said phase transfer catalyst from said aqueous phase by extraction with o-dichlorobenzene.

2. A method according to claim 1 wherein the amount of inorganic salt dissolved in the aqueous phase is at least about 35 grams per 100 ml.

3. A method according to claim 2 wherein the inorganic salt is sodium nitrite.

4. A method according to claim 1 wherein extraction with o-dichlorobenzene is effected at a temperature above about 65° C.

5. A method according to claim 4 wherein the amount of inorganic salt dissolved in the aqueous phase is at least about 35 grams per 100 ml.

6. A method according to claim 5 wherein the inorganic salt is sodium nitrite.

7. A method according to claim 1, 3, 4, or 6 wherein the phase transfer catalyst is at least one compound selected from the group consisting of tetraalkylammonium halides, tetraarylphosphonium halides and crown ethers.

8. A method according to claim 1 wherein the phase transfer catalyst is at least one of tetrabutylammonium bromide, tetraethylammonium bromide, tetraphenylphosphonium bromide and 18-crown-6.

9. A method according to claim 8 wherein the phase transfer agent is tetrabutylammonium bromide.

10. A method according to claim 8 wherein the substituted phthalimide is 4-nitro-N-methylphthalimide.

11. A method according to claim 10 wherein the alkali metal salt of the hydroxyaromatic compound is the disodium salt of bisphenol A.

12. A method according to claim 11 wherein the phase transfer agent is tetrabutylammonium bromide.

13. In a method for preparing 2,2-bis[4-(N-methylphthalimide-4-oxy)phenyl]propane by the nucleophilic displacement reaction of 4-nitro-N-methylphthalimide with the disodium salt of bisphenol A in the presence of tetrabutylammonium bromide as a phase transfer catalyst followed by aqueous extraction, the improvement which comprises:
(A) conducting said displacement reaction in o-dichlorobenzene as diluent, and
(B) dissolving sodium nitrite in the aqueous phase in an amount of at least about 75 grams per 100 ml. and extracting the same with o-dichlorobenzene at a temperature about about 65° C., thereby recovering a substantial amount of said phase transfer catalyst.

* * * * *